US009833353B2

(12) United States Patent
Witt et al.

(10) Patent No.: US 9,833,353 B2
(45) Date of Patent: Dec. 5, 2017

(54) GLOSSOPLASTY IMPLANT TENSION RELIEF SYSTEM

(75) Inventors: Erik Kurt Witt, Wyckoff, NJ (US); Charles Thomas, Monroeville, PA (US)

(73) Assignee: Koninklijke Philips N.V., Eindhoven (NL)

(\*) Notice: Subject to any disclaimer, the term of this patent is extended or adjusted under 35 U.S.C. 154(b) by 473 days.

(21) Appl. No.: 13/701,201

(22) PCT Filed: Apr. 28, 2011

(86) PCT No.: PCT/IB2011/051890
§ 371 (c)(1),
(2), (4) Date: Feb. 19, 2013

(87) PCT Pub. No.: WO2011/151745
PCT Pub. Date: Dec. 8, 2011

(65) Prior Publication Data
US 2013/0233324 A1    Sep. 12, 2013

Related U.S. Application Data

(60) Provisional application No. 61/351,068, filed on Jun. 3, 2010.

(51) Int. Cl.
*A61F 5/56* (2006.01)
*A61B 17/04* (2006.01)
*A61B 17/00* (2006.01)

(52) U.S. Cl.
CPC ............ *A61F 5/56* (2013.01); *A61B 17/0401* (2013.01); *A61F 5/566* (2013.01); *A61B 2017/00814* (2013.01); *A61B 2017/044* (2013.01); *A61B 2017/0419* (2013.01); *A61B 2017/0427* (2013.01); *A61B 2017/0464* (2013.01); *A61B 2017/0496* (2013.01)

(58) Field of Classification Search
USPC ........... 128/848, 859–862; 433/6–7; 602/902
See application file for complete search history.

(56) References Cited

U.S. PATENT DOCUMENTS 5,988,171 A * 11/1999 Sohn .................. A61B 17/0401
                                                    128/848
7,337,781 B2    3/2008 Vassallo
(Continued)

FOREIGN PATENT DOCUMENTS

CN    101389288 A    3/2009
CN    101583327 A    11/2009
(Continued)

*Primary Examiner* — Ophelia A Hawthorne

(57) ABSTRACT

A glossoplasty implant tension relief system for treating an airway of a patient has a first portion configured to engage a mandible of the subject. The system also has a second portion configured to engage a tongue of the subject to retain at least a portion of the tongue. The system includes a connecting portion configured to connect the first portion and the second portion. The connecting portion is constructed and arranged to provide tension between the first portion and the second portion. The connecting portion includes an i) inelastic portion and ii) an elastic portion configured to provide elasticity between the first portion and the second portion.

21 Claims, 10 Drawing Sheets

(56) References Cited

U.S. PATENT DOCUMENTS

| | | | |
|---|---|---|---|
| 8,037,885 B2* | 10/2011 | Metzger | A61F 2/00 128/848 |
| 8,096,303 B2* | 1/2012 | Dineen | A61B 17/0401 128/848 |
| 2006/0207608 A1 | 9/2006 | Hirotsuka et al. | |
| 2006/0235264 A1* | 10/2006 | Vassallo | 600/37 |
| 2007/0137654 A1 | 6/2007 | Paraschac et al. | |
| 2008/0035160 A1 | 2/2008 | Woodson et al. | |
| 2008/0066764 A1 | 3/2008 | Paraschac et al. | |
| 2010/0004659 A1* | 1/2010 | Hegde | A61F 5/566 606/99 |

FOREIGN PATENT DOCUMENTS

| | | |
|---|---|---|
| EP | 1216013 B1 | 6/2006 |
| JP | 2002506376 A | 2/2002 |
| JP | 2004154583 A | 6/2004 |
| JP | 2008529608 A | 8/2008 |
| WO | 2007092865 A2 | 8/2007 |

* cited by examiner

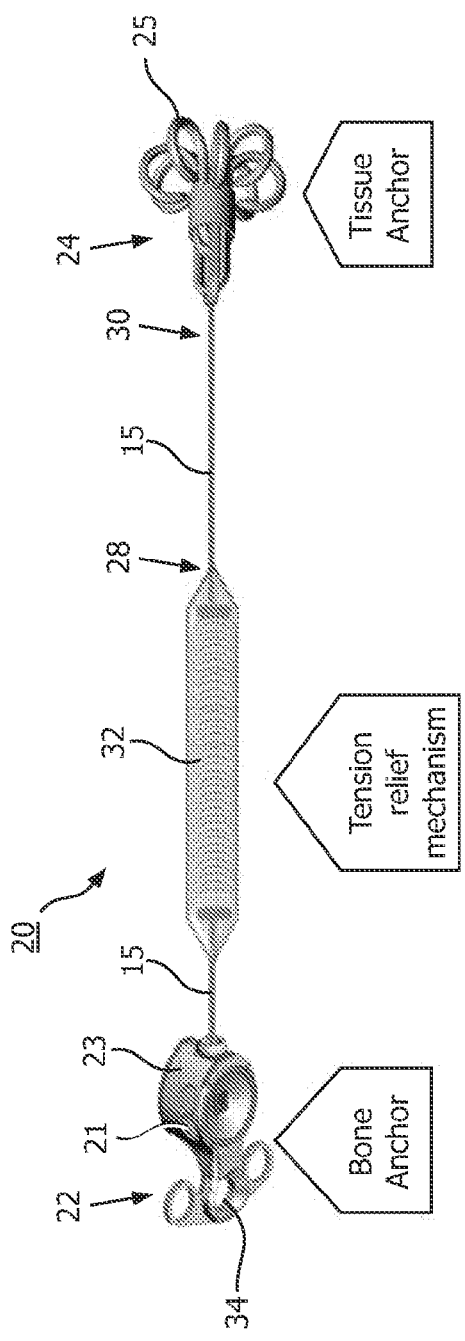
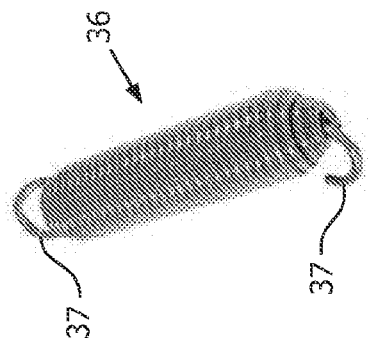
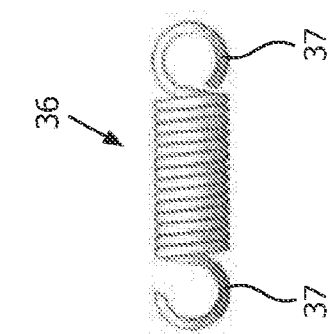
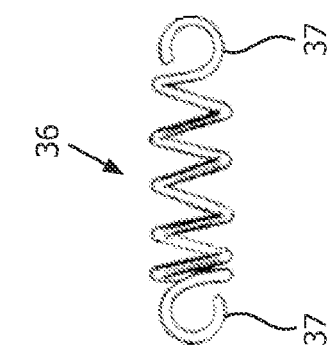
FIG. 4
FIG. 5A
FIG. 5B
FIG. 5C

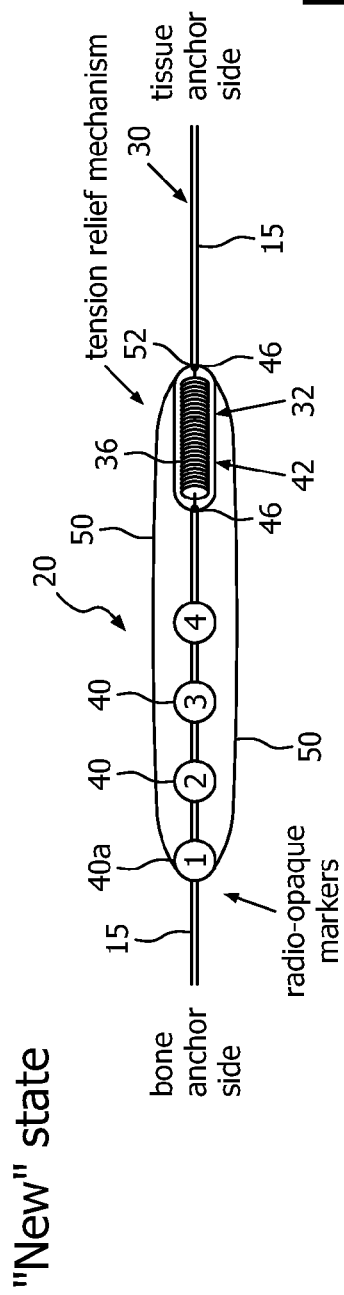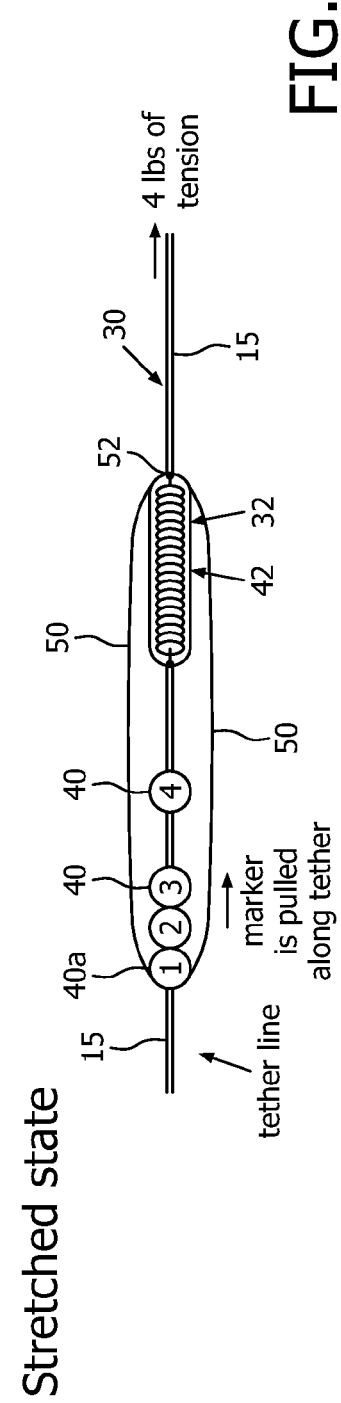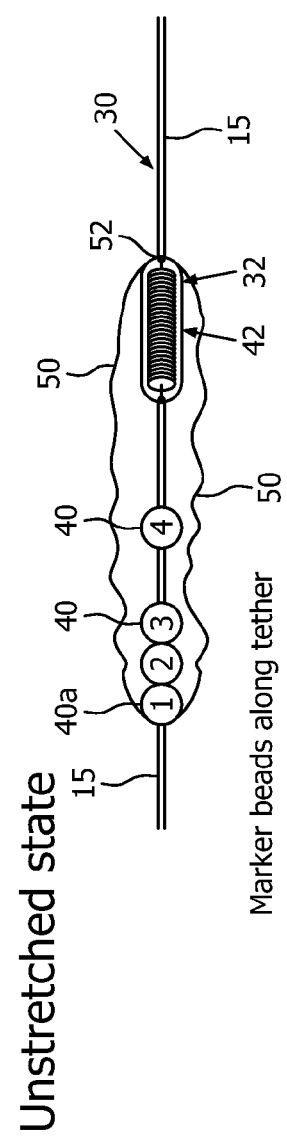

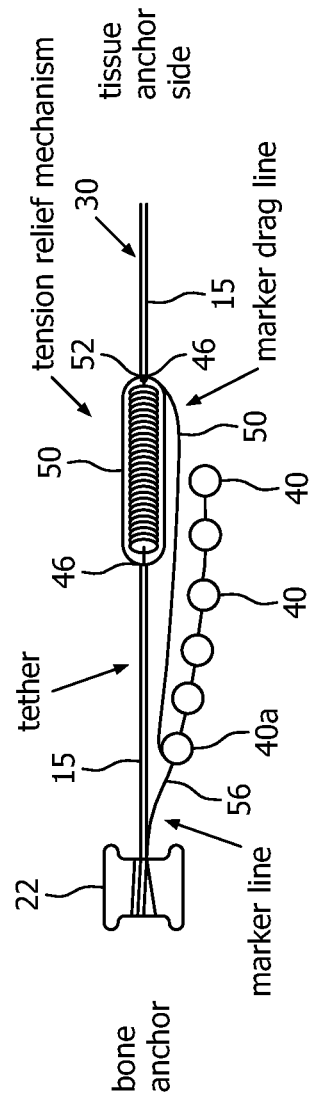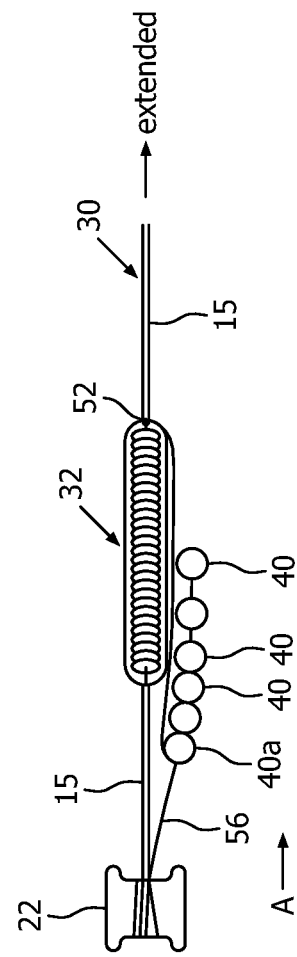
FIG. 11A
FIG. 11B

GLOSSOPLASTY IMPLANT TENSION RELIEF SYSTEM

BACKGROUND

1. Field

The invention relates to a glossoplasty implant tension relief system and the use thereof as a method for treating a condition of an airway of a patient.

2. Description of the Related Art

Obstructive Sleep Apnea (OSA) is a sleep disorder that affects millions of people worldwide. For example, approximately 17 million people in the United States and approximately 20 million people in Europe are affected by OSA. In fact, many patients who have sleep apnea have not yet been diagnosed.

OSA is a condition characterized by frequent obstruction of an individual's airway during sleep. People with OSA may exhibit symptoms including excessive daytime sleepiness, loud snoring, labored breathing, morning headaches, loss of energy, lack of concentration, and irritability. For people experiencing OSA, their tongue may be displaced posteriorly during sleep as a consequence of reduced muscle activity. The displaced tongue may push the soft palate posteriorly and may seal off at least portions of the airway.

Untreated OSA has been associated with serious health consequences such as hypertension, myocardial infarction, cerebrovascular disease, cardiac arrhythmias and sudden death. Treatment of OSA can lead to the improvement of patient symptoms and the improvement of key respiratory variables, such as, for example, the Apnea/Hypopnea Index (AHI) and the lowest oxygen saturation (LSAT).

Continuous Positive Airway Pressure (CPAP) devices are often used as first-line treatments and are the most common treatments for OSA. Although CPAP therapy is highly effective in treating OSA if used properly, patient compliance with these devices are low due to several reasons. For example, nasal masks may be ineffective for some patients, such as those who sleep with their mouths open. Patients may also experience discomfort and the inability to sleep while using the CPAP device. The use of CPAP can lead to other complications, such as local skin irritation, nasal and throat dryness, and eye irritation. More than 50% of diagnosed OSA patients do not adequately use CPAP. Accordingly, patients often abandon therapy during the first 2 to 4 weeks of treatment.

Alternative treatments for OSA include surgical treatments, which avoid problems with patient compliance. The most common current surgical therapies for OSA targets the soft palate and are very painful for patients. The placement of the tongue is a major factor of OSA and there are currently few surgical options to treat tongue collapse.

Implantable devices (e.g., Aspire Advance™ System, Medtronic/InfluENT Repose® Tongue Suspension) have been developed to prevent collapse of the tongue into the airway during sleep. These devices are intended to offer the treating physician a means to surgically treat obstructive sleep apnea in appropriate patients. Generally, some of these devices bias at least a portion of the base of the tongue in a generally anterior/lateral direction to prevent obstruction of the airway. This bias may be created by changing the distance or tension between a portion of the patient's tongue and the patient's mandible.

The Advance™ System, an example of which is shown in FIG. 1, consists of a soft tissue anchor 2, which is delivered into the genioglossus muscle 7 with a specially designed access and delivery system, and an adjustable bone anchor 4, which is attached to the base of the mandible 3 with standard bone screws 5. The tissue anchor 2 is attached to the bone anchor 4 with a tether line 6. The Advance™ System is designed to stabilize the tongue 9 in an anteriorly advanced position, thereby enlarging and increasing the size and stability of the airway 11 in patients diagnosed with obstructive sleep apnea. As the tongue 9 is stabilized, the compliance of the tongue 9 in the anterior/posterior direction is reduced and increased airway stability is achieved.

The Repose Tongue Suspension, an example of which is shown in FIG. 2, is attached to the base of the mandible 3 with standard bone screws 12 (see FIG. 3 for clearer view). A suture loop 18 is connected to the bone anchor 10. One end of the suture loop 18 is inserted through two locations 14, 16 in the posterior portion of the tongue 9. The two ends of the suture loop 18 are then tied to advance and stabilize the genioglossus muscle to prevent the tongue from falling back and obstructing the patient's airway.

Although tongue implants may be effective in preventing the collapse of the tongue into the airway, there are problems associated with the current tongue implants. Tongue implants that engage soft tissue have to contend with passive and active states of the tongue. During sleep, the genioglossus muscle, which runs from the front of the lower jaw into the tongue from tip to base, has a range of activation states. This range includes being mostly passive during deep sleep to being partially activated during light sleep. In these states, a device only needs to support the passive weight of the tongue, which may be one or two pounds. The tongue, in a passive state, does not become an obstruction if it is prevented by the implant device from collapsing into the patient's airway. Furthermore, the force of inhalation does not usually pose a problem for the implantable device. That is, the implantable device may perform as intended when the force of inhalation is exerted on the obstructing tongue and the implantable device. In contrast, forces that are generated during swallowing can exceed 5 to 6 pounds. Swallowing is an activity that a patient performs when awake (or during an arousal from sleep) and does not usually result in airway obstruction. However, the implant must nevertheless retain its properties and position during activities, such as swallowing, that generate forces on the tongue and the implant device. As such, the devices must have an adequate and flexible design margin that allows them to operate in such extreme cases. The devices must also be able to be adjusted before, during, and/or after the device has been implanted into the patient such that the device can be customized for the patient and can accommodate changing conditions.

This range of forces that are exerted on the implant devices poses a challenge for existing devices. In some situations, soft tissue of the tongue can be damaged due to small tissue volume that is captured by the tissue anchor when extreme forces are exerted on the device. Although there are implants that are designed to operate in extreme forces, these devices tend to be larger, bulkier, and more difficult to implant and deploy than their smaller, conventional counterparts. Thus, there is a need for an improved implant system.

SUMMARY

One aspect of the invention relates to a glossoplasty implant tension relief system having a first portion configured to engage a mandible of the subject and a second portion configured to engage a tongue of the subject to retain at least a portion of the tongue. The system also includes a connecting portion configured to connect the first portion and the second portion. The connecting portion is constructed and arranged to provide tension between the first portion and the second portion. The connecting portion includes an i) inelastic portion and ii) an elastic portion configured to provide elasticity between the first portion and the second portion.

Another aspect relates to a method for treating a condition of an airway of a subject. The method include the steps of engaging a first portion of an implantable device system with a mandible of a subject and engaging a second portion of the implantable device system with a tongue of the subject to retain at least a portion of the tongue, thereby reducing obstruction of the airway of the subject by the tongue. The method also includes the step of providing tension between the first portion and the second portion, wherein tension is provided by a connecting portion, the connecting portion including an inelastic portion and an elastic portion. The method also includes the step of providing elasticity between the first portion and the second portion, wherein elasticity is provided by the elastic portion of the connecting portion.

Another aspect relates to a glossoplasty implant tension relief system having means for engaging a first portion of an implantable device system with a mandible of a subject and means for engaging a second portion of the implantable device system within a tongue of the subject to retain at least a portion of the tongue, thereby reducing obstruction of the airway of the subject by the tongue. The system also has means for providing tension between the first portion and the second portion, wherein tension is provided by a connecting portion. The connecting portion includes an inelastic portion and an elastic portion. The system also includes means for providing elasticity between the first portion and the second portion, wherein elasticity is provided by the elastic portion of the connecting portion.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. In one embodiment of the invention, the structural components illustrated herein are drawn to scale. It is to be expressly understood, however, that the drawings are for the purpose of illustration and description only and are not a limitation of the invention. In addition, it should be appreciated that structural features shown or described in any one embodiment herein can be used in other embodiments as well. It is to be expressly understood, however, that the drawings are for the purpose of illustration and description only and are not intended as a definition of the limits of the invention. As used in the specification and in the claims, the singular form of "a", "an", and "the" include plural referents unless the context clearly dictates otherwise.

BRIEF DESCRIPTION OF THE DRAWINGS

FIG. 4 illustrates a perspective view of an implant system in accordance with an embodiment of the present invention;

FIGS. 5A-5D illustrate perspective views of components of an elastic portion of the implant system in accordance with embodiments of the present invention;

FIGS. 10A-10C illustrate a detailed view of the elastic portion of the implant system having tension indicators in accordance with another embodiment of the present invention;

FIGS. 11A-11B illustrate a detailed view of the elastic portion of the implant system having tension indicators in accordance with another embodiment of the present invention;

DETAILED DESCRIPTION OF EXEMPLARY EMBODIMENTS

Figure 1:
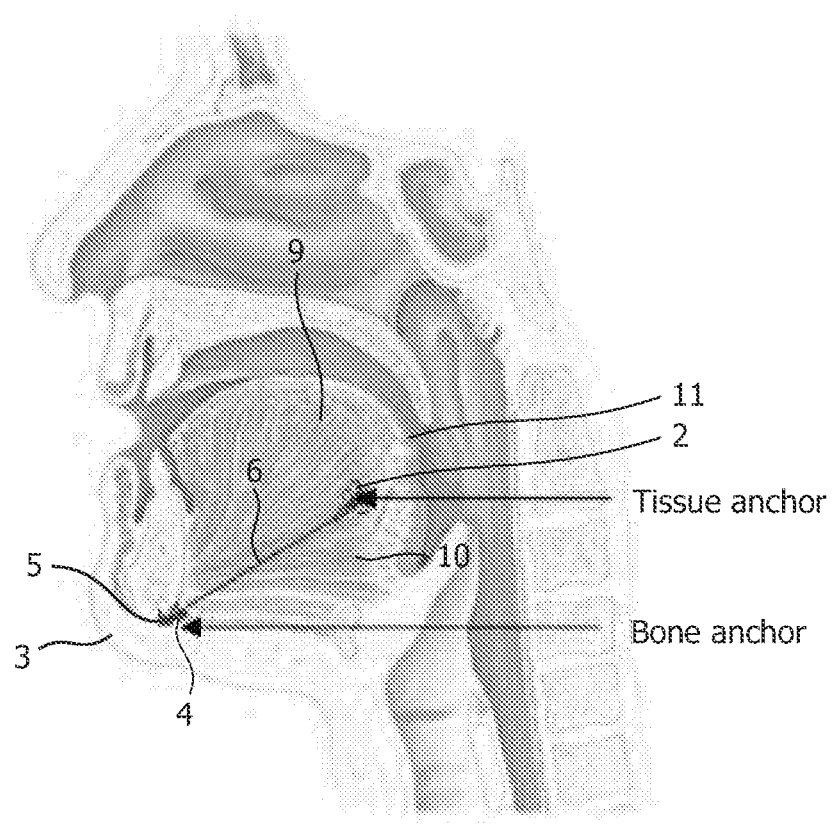
FIG. 1 illustrates a side sectional view of a patient having a conventional tongue implant device implanted therewithin.
Figure 2:
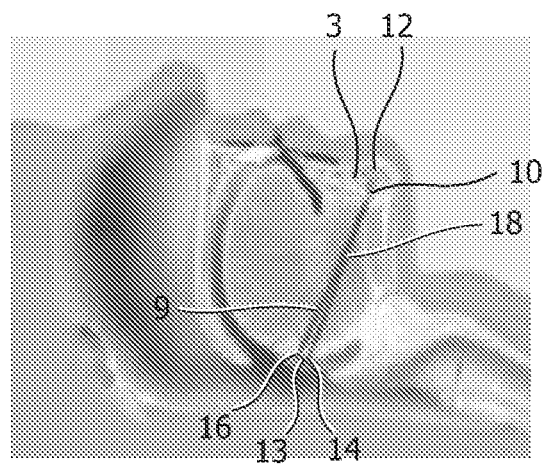
FIG. 2 illustrates a side sectional view of a patient in a supine position having a conventional tongue implant implanted therewithin.
Figure 3:
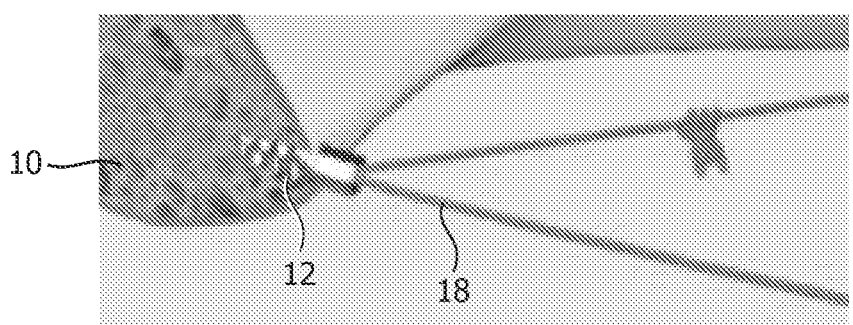
FIG. 3 illustrates a detailed view of a portion of a conventional tongue implant device.

FIG. 4 illustrates a glossoplasty implant tension relief system 20 in accordance with an embodiment of the present invention. The glossoplasty implant tension relief system 20 has a first portion 22 configured to engage the mandible of the subject and a second portion 24 configured to engage the tongue of the subject to retain at least a portion of the tongue. A connecting portion 28 is constructed and arranged to connect the first portion 22 and the second portion 24 and to provide tension between the first portion 22 and the second portion 24. The connecting portion 28 includes an i) inelastic portion 30 and ii) an elastic portion 32 configured to provide elasticity between the first portion 22 and the second portion 24.

Figure 14:
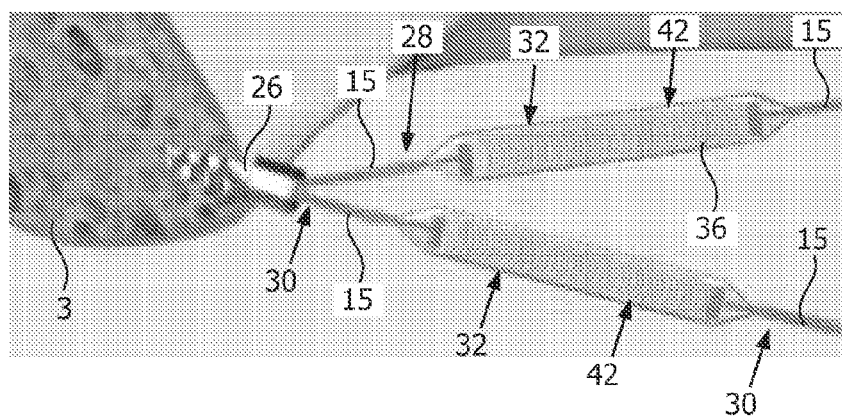
FIG. 14 illustrates a detailed view of a portion of the implant system in accordance with an embodiment of the present invention.

The first portion 22 may include a bone anchor 23 attached to the mandible with an attachment mechanism, such as, for example, a bone screw 26 (see FIG. 14). However, this example is not intended to be limiting and it is contemplated that other attachment mechanisms, such as clips, threaded bolts, staples, pins, or suture material looped around or through the mandible may be used. In one embodiment, the bone screws 26 may be inserted through apertures 34 provided on the bone anchor 23 to attach the bone anchor 23 to the mandible of the subject. The bone screws 26 may optionally be made of titanium alloy. The first portion 22 may also optionally include just the attachment mechanism, such as the bone screw 26, without a bone anchor 23, as shown in FIG. 14.

Referring again to FIG. 4, in some embodiments, the second portion 24 includes a tissue anchor 25 made of materials such as titanium alloy, Nitinol alloy, other materials, or a combination thereof. As was mentioned above, second portion 24 is configured to engage the tongue of the subject to hold the tongue of the subject out of the airway of the subject during sleep.

It is contemplated that the connecting portion 28 may include more than one inelastic portion 30 and/or more than one elastic portion 32. The elastic portion 32 is configured to be elastically flexible, while the inelastic portion 30 is configured to be significantly less flexible than elastic portion 32 (e.g., substantially inflexible). The inelastic portion(s) 30 and the elastic portion(s) 32 may be arranged in a variety of configurations. In some embodiments, the second portion 24 and the inelastic portion 30 of the connecting portion 28 may be made of the same material and/or structure. For example, in one embodiment, the inelastic portion 30 may include a portion of a tether 15 and the second portion 24 may include another portion of the tether 15 that is inserted through the tongue to retain the tongue.

In one embodiment, the first portion 22 includes the bone anchor 23 having an adjustment mechanism 21 directly attached to the bone anchor 23. The adjustment mechanism 21 may optionally reside on the proximal head portion of the bone anchor 23. The adjustment mechanism 21 may include a spool or rotation assembly (not shown) for adjusting the length of the connecting portion 28 and the tension of the inelastic portion 30 between the first portion 22 and the second portion 24. The spool or rotation assembly may optionally include a spool lock that allows the rotation of the spool to take up or release a portion of the connecting portion 28 when desired, while resisting unintentional uptake or release of the connecting portion 28 at other times. When titration is required, a titration needle may be inserted through an incision and into the bone anchor 23 to adjust the tension or length of the connecting portion 28 by rotating the spool assembly.

In some embodiments, the second portion 24 may include any of a variety of structures capable of engaging the surrounding tissue. For example, the second portion 24 may include a tissue anchor 25 having sharp or blunt tissue grasping or engagement structures that facilitate the engagement to the surrounding tissue. The tissue anchor 25 may also optionally have barbs, angled pins, hooks, or other angled or ramped surfaces constructed and arranged to incline radially outwardly from a distal to proximal direction. In the embodiment shown in FIG. 4, the tissue anchor 25 includes tissue grasping or engaging structures that radiate outwardly to engage surrounding tissue. The tissue anchor 25 may be self-expandable or may require external force to expand so that the tissue anchor 25 can engage the surrounding tissue. For example, the tissue anchor 25 may self-expand once it is released from a delivery tool (not shown), or the tissue anchor 25 may expand after tension has been applied thereto by the connecting portion 28. In another embodiment, the tissue anchor 25 may be a loop of suture material inserted into the tongue. A hypodermic needle or other piercing delivery tools may be used to implant the second portion 24 percutaneously into the tongue.

In the embodiment shown in FIG. 4, the inelastic portion 30 may include the tether 15 used to fix the distance between the first portion 22 and the second portion 24. The tether 15 may be made of Nitinol, steel, tantalum, other materials, or a combination thereof. The inelastic portion 30 may optionally be coated with a lubricating biocompatible coating or a bioabsorbable coating that may cause scar or connective tissue formation around the inelastic portion 30. The formation of scars or connective tissues may facilitate the effect of the implant system 20 by resisting movement of the inelastic portion 30. It is appreciated that the features of the inelastic portion 30, such as the particular material used, the diameter, the length, the cross-sectional shape, may be based upon factors such as the patient's personal characteristics or desired effect. It is appreciated that in some embodiments, there may not be continuous tension present in the inelastic portion 30. That is, in such embodiments, tension may be generated in the inelastic portion 30 when the tongue has been displaced a certain distance and/or a certain range of directions. In some embodiments, the tension in the inelastic portion 30 may be adjusted during implantation by spooling the inelastic portion 30 onto the bone anchor 23 using an adjustor tool. Implantation of the implant system 20 will be described in more detail later.

The elastic portion 32 may be provided in-line or in series with the inelastic portion 30. In some embodiments, the elastic portion 32 may be directly connected to the inelastic portion 30. In some embodiments, the elastic portion 32 may be made of elastic materials, such as rubber (silicone), polymers, or other materials that provide elasticity. In some embodiments, the elastic portion 32 may include materials that are shaped or formed into elastic configurations. In some embodiments, the elastic portion 32 may include materials such as stainless steel, shape memory alloys, or other materials that can be shaped into structures that have spring-like properties to absorb tension. In some embodiments, various springs may be used. It is also contemplated that the elastic portion 30 of the implant system 20 may include any combinations of elastic materials or structures that provide elasticity. Some embodiments may include parallel configurations, such as wherein the inelastic portion 30 is parallel to the elastic portion 32. This configuration may serve as a limit to the amount of stretch the elastic portion 32 could undergo. For example, in embodiments where a spring is used, the inelastic portion 30 can prevent the spring from stretching beyond its elastic limit.

Figure 5D:
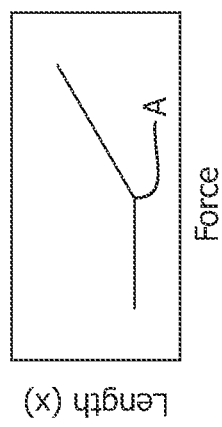

The elastic portion 32 may include tension or extension springs 36 (see FIGS. 5A-5C), such as helical or coil springs, that are fixed in length when in a default, free state and which may be extended when a tension threshold is exceeded. Typically, the coils of the coiled springs are touching in the resting state. The extension spring may extend in a linear or non-linear fashion when force is applied thereto. Some springs (an example of which is shown in FIG. 5D) may also have stops, tethers, or other structures that prevent over-extension thereof. The springs 36 may have attachment structures 37, such as hooks or eyes, at each end that enables the springs 36 to be attached to other structures, such as the inelastic portion 30 of the connecting portion 28.

Figure 6:
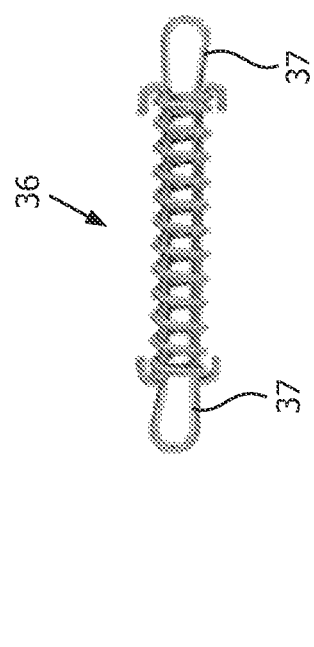
FIG. 6 illustrates the relationship between force and length of extension of a spring of the elastic portion.

Extension springs are typically manufactured with an initial tension Fi which presses the coils together in the default, free state. Once the tension threshold is overcome, the spring behaves linearly. The extension spring 36 may behave in accordance with the following equation 1.1:

$$TF = IT + D \times k \qquad \text{(Eq. 1.1)}$$

where:
TF=total force exerted on spring
D=distance spring is deflected
IT=initial tension force on spring k=spring constant determined by experiment or calculation The relationship between the force applied to the spring 36 and the length of the spring 36 is illustrated in FIG. 6. FIG. 6 shows that the length of the spring 36 does not increase (in other words, the spring does not extend) until the force applied thereto has exceeded a certain threshold at point A. After the threshold has been exceeded, the spring 36 then extends in a linear fashion.

Figure 7:
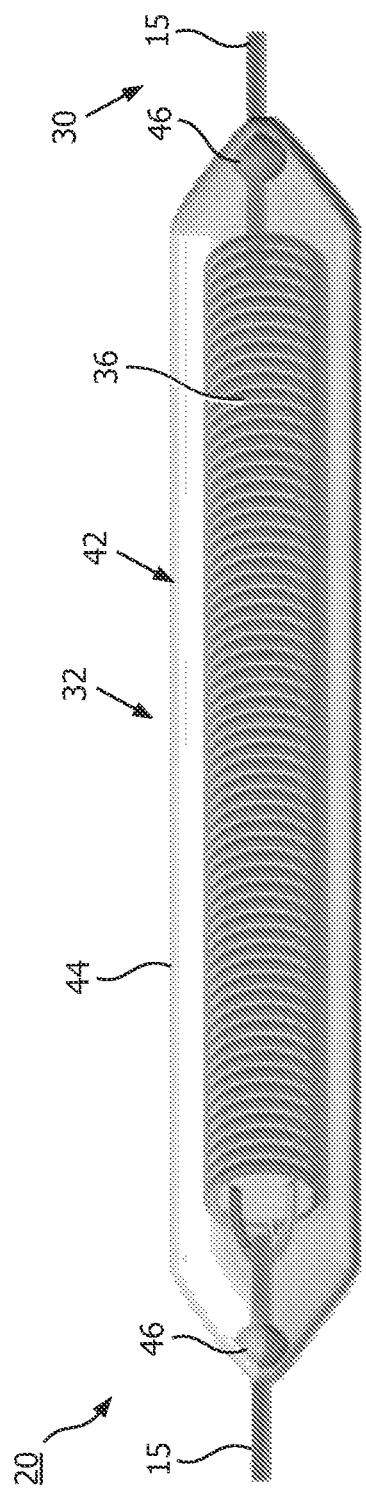
FIG. 7 illustrates a perspective view of the elastic portion of the implant system in accordance with an embodiment of the present invention.

FIG. 7 shows another example of the spring 36 that may be used in the elastic portion 32 of the connecting portion 28 of the implant system 20. FIG. 7 shows a spring arrangement 42 having the spring 36 encapsulated in a hollow sleeve 44 with sealed ends 46. The sleeve 44 may be made of silicone or other materials. The spring arrangement 42 may comprise concentric rings of silicone with different durometers. The spring arrangement 42 may be positioned anywhere on the connecting portion 28, including adjacent to either the bone anchor 23 of the first portion 22 or the tissue anchor 25 of the second portion 24. Encapsulating the elastic portion 32 may prevent the soft tissue of the tongue from becoming ensnared in a portion of the elastic portion 32. It is contemplated that either one or both of the elastic portion 32 and the inelastic portion 30 of the connecting portion 28 may be encapsulated.

Figure 8:
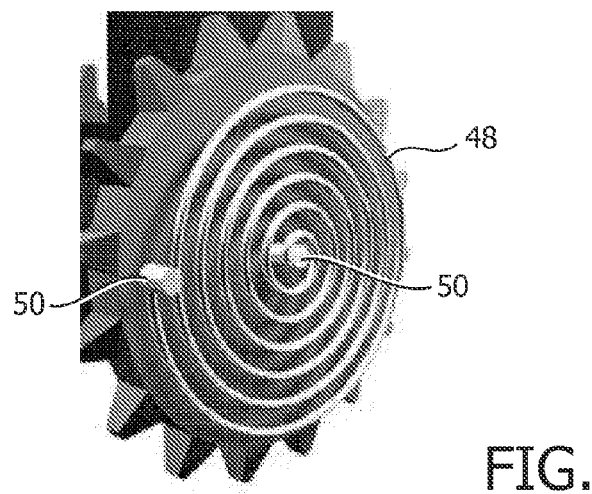
FIG. 8 illustrates a perspective view of a component of the elastic portion of the implant system in accordance with another embodiment of the present invention.

In some embodiments, the elastic portion 32 of the connecting portion 28 may include a torsion spring 48 (see FIG. 8). Torsion springs are designed to be twisted rather than compressed or extended. The torsion spring 48 may include attachment ends 50 that enable the torsion spring 48 to be attached to other structures, such as the inelastic portion 30 of the connecting structure 28 when the elastic portion 32 is provided in-line or in series with the inelastic portion 30. As such, the torsion spring 48 enables the length of the connecting portion 28 to be increased to relieve tension thereon when the tension of the connecting portion 28 exceeds a predetermined threshold. The torsion spring 48 is constructed and arranged to pull the connecting portion 28 back (or decrease the length of the connecting portion 28) when the force causing the excess tension has subsided.

Alternatively or additionally, a second torsion spring 48 may be provided in the bone anchor 23. In one embodiment, one end 50 of the torsion spring 48 is attached to the spool assembly of the bone anchor 22 while another end 50 of the torsion spring 48 is attached to the connecting portion 28. When the tension in the connecting portion 28 exceeds a predetermined threshold, the spool assembly can be rotated to increase the length of the connecting portion 28 so that tension on the connecting portion 28 and the rest of the implant system 20 can be relieved. The rotation of the spool assembly may wind the torsion spring 48, which can then pull the connecting portion 28 back (or decrease the length of the connecting portion 28) when the force causing the excess tension has decreased. It is contemplated that any combination and number of torsion springs 48 may be used as part of the connecting portion 28 and/or the bone anchor 23.

The forces that the implant system 20 may be subjected to by the tongue may vary from subject to subject. Accordingly, it may be desirable for clinicians or other healthcare providers to be able to realize the maximum amount of force that has been exerted on the implant systems 20. For embodiments of the implant systems 20, the implant system 20 might not have a power source and thus alternative techniques are used. Accordingly, in some embodiments, x-ray fluoroscopy (or other imaging techniques, such as planar x-ray, ultrasound, magnetic resonance imaging (MRI), computed tomography (CT) scan) can be used to detect the force that has been applied to the implant system 20 based on the maximum extension of the implant system 20.

In some embodiments, the implant system 20 is provided with tension indicators or markers 40 (see FIG. 9A), such as rings, beads, or any structure that can slide along the implant system 20 when the implant system 20 is extended. The markers may be radio-opaque wherein visibility of the markers is achieved using any imaging modality. The markers 40 may be arranged in a default position before an initial extension of the connecting portion 28. The markers 40 may be constructed and arranged to be pulled along the implant system 20 in one direction when the connecting portion 28 is extended due to excess tension. The markers 40 may be arranged in a second position as a result of the movement due to the extension of the connecting portion 28. When the tension is relaxed and is again below the predetermined threshold, the connecting portion 28 may be pulled back (or decreased in length), but the markers may retain its second position. That is, after the markers 40 have been moved to their second position, the markers 40 may remain in that second position. However, if another force exerted on the implant system 20 is greater than the previous force and causes the connecting portion 28 to extend more than the last extension, the markers 40 may be moved further in the one direction. Accordingly, more markers 40 may be compressed as a result of the extra extension due to the increased force. Thus, the final position or arrangement of the markers 40 indicate the maximum extension of the connecting portion 28 and also the maximum tension to which the implant system has been subjected.

Figure 9A:
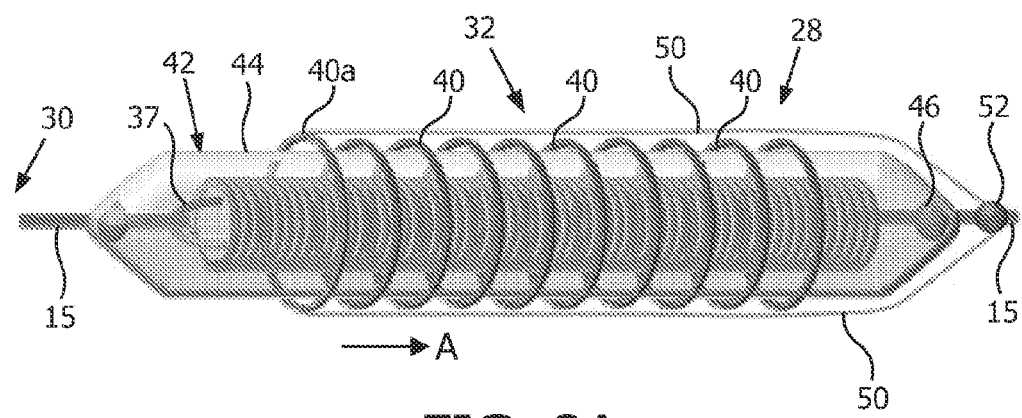
FIGS. 9A-9B illustrate a perspective view of the elastic portion of the implant system having tension indicators in accordance with an embodiment of the present invention.

FIG. 9A illustrates an embodiment of the connecting portion 28 of the implant system 20. The elastic portion 32 includes the spring arrangement 42 having the tension spring 36 encapsulated within the silicone sleeve 44. Each end 46 of the sleeve 44 is operatively connected to the inelastic portion 30, and each end 37 of the spring 36 is operatively connected to the inelastic portion 30. In the illustrated embodiment, markers 40, taking the form of rings, are provided on the silicone sleeve 44 in a pre-arranged configuration. In the illustrated embodiment, the markers 40 surround the periphery of the silicone sleeve 44. The arrangement and configuration of the markers 40 shown in FIG. 9A is the default "initial" position of the markers before the connecting portion 28 has been extended for the first time. The connecting portion 28 may have a default length— the length before the connecting portion 28 is extended due to increased tension above the predetermined threshold. It is appreciated that the configuration and arrangement of the markers 40 may vary in other embodiments and/or may be customized for each subject. In the illustrated embodiment, one end of a pulling assembly 50 is attached to a first marker 40a and another end of the pulling assembly 50 is attached to a reference location 52 on the connecting portion 28. In this embodiment, the reference location 52 is on the inelastic portion 30, although it is contemplated that the reference location 52 may be located at other locations or components of the implant system 20. The pulling assembly 50 is constructed and arranged to pull the first marker 40a in the direction of A (see FIG. 9A) when the connecting portion 50 is extended. The first marker 40a is constructed and arranged to compress other markers 40 and to push them in the direction of A.

Figure 9B:
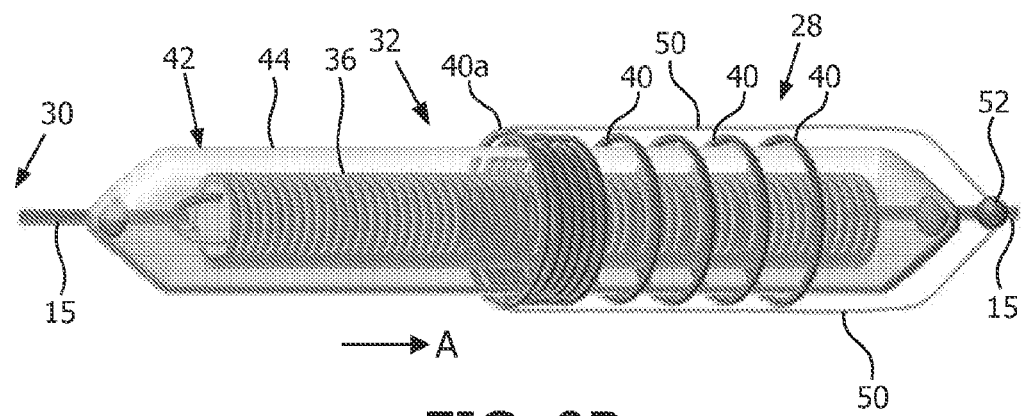

When tension is applied to the connecting portion 28 and the tension exceeds the predetermined threshold, the elastic portion 32 may extend to relieve the tension. As the elastic portion 32 extends, the markers 40 may be pulled to their second position by the pulling arrangement 50 in the direction of A (see FIG. 9A). In this embodiment, the markers 40 can only be moved in the direction of A. Some of the markers 40, including marker 40a, may become compressed in this second position or arrangement, as shown in FIG. 9B. After the tension subsides and the elastic portion 32 is retracted such that the length of the connecting portion 28 is decreased back to its default length, the markers 40 may still retain this second arrangement. FIG. 9B illustrates the connecting portion 28 of the implant system 20 after the connecting portion 28 has been extended and the markers 40 have been moved to their second arrangement. In the illustrated embodiment, the markers 40 have been moved from their initial position to this second position wherein some of the markers 40 are compressed.

FIGS. 10A-10C illustrate another embodiment of the connecting portion 28 having markers 40 to indicate maximum tension. The markers 40, taking the form of radio-opaque beads in this embodiment, are arranged along the inelastic portion 30 of the connecting portion 28. The pulling assembly 40 is attached to the reference point 52 at one end and to the first marker 40a at the other end. The spring assembly 42 is provided between the markers 40 and the reference point 52. In the illustrated embodiment, the reference point 52 is located closer than the first marker 40a to the tissue anchor 25, and the first marker 40a is located closer than the reference point 52 to the bone anchor 23. Each end 46 of the sleeve is connected to the inelastic portion 30.

FIG. 10A illustrates the markers 40 in the initial state before the connecting portion 28 has been extended. The markers 40 are arranged in their initial, default configuration or position. The spring arrangement 42, which forms the elastic portion 32, is in its initial, default position and the connecting portion 28 has a default, initial length. After a force (e.g., 4 lbs) exceeding the predetermined threshold has been applied to the implant system 20, and the connecting portion 28 is extended in response to the force to relieve the tension thereon, the pulling assembly 52 pulls the marker 40a in the direction of A, as shown in FIG. 10B. The marker 40a then pushes and compresses the other markers in the direction of A so that the markers 40 are moved to their second configuration. The more force that is applied to the implant system 20, the more markers 40 that are compressed. After the force applied to the implant system 20 has subsided, the spring arrangement 42 then returns to its initial, default position and the length of the connecting portion 28 is decreased to its default, initial length, as shown in FIG. 10C. However, the markers 40 retain their second configuration even after the force applied thereto has been relieved. This second configuration indicates the maximum tension to which the implant system 20 has been subjected.

If more tension (greater than the previous tension) is generated on the implant system 20, then the connecting portion 28 may extend more than the previous distance, and as such, more markers 40 may compress. That is, increased tension causes the pulling assembly 50 to pull the marker 40a further in the direction of A. Accordingly, the final configuration or arrangement of the markers 40 may indicate the maximum tension.

FIGS. 11A and 11B illustrate another embodiment of the connecting portion 28 having markers 40 to indicate maximum tension. As shown in FIG. 11A, the markers 40, taking the form of beads in this embodiment, are provided on a marker line 56 instead of on the inelastic portion 30. The markers 40 are arranged in their initial, default position between the bone anchor 22 and the reference point 52 on the inelastic portion 30. The spring arrangement 42, which forms the elastic portion 32, is in its initial, default position and the connecting portion 28 has a default, initial length. One end of the marker line 50 is connected to the bone anchor 24 and the other end may hang freely (without connecting to any structures) or may connect to other appendages. Each end 46 of the spring arrangement 42 is connected to the inelastic portion 30. The pulling arrangement 50 is attached to the reference point 52 on the inelastic portion 30 at one end and to the first marker 40a at the other end.

After a force exceeding the predetermined threshold has been applied to the implant system 20, and the connecting portion 28 is extended in response to the force to relieve the tension thereon, the pulling assembly 52 pulls the marker 40a in the direction of A. The marker 40a then pushes and compresses the other markers 40 in the direction of A until the markers 40 are moved to their second configuration, as shown in FIG. 11B. The more tension that is applied, the more markers 40 that are compressed. After the tension has subsided, the spring arrangement 42 then returns to its initial, default position and the length of the connecting portion 28 is decreased to its default, initial length. The markers 40 retain their second configuration even after the force applied to the implant system 20 is decreased. This second configuration indicates the maximum tension to which the implant system 20 has been subjected. Similar to the embodiments above, the markers 40 may be further compressed to attain another arrangement that indicates the maximum tension to which the implant system 20 has been subjected.

X-ray or other observation methods can be used to count the number of markers 40 and/or measure the distance the markers 40 have moved. Counting the number of markers 40 may provide an accurate measure of distance that the connecting portion 32 has been extended. By knowing the relationship between tension (or force) and distance of extension, the distance measure obtained from analyzing the markers 40 can be used to calculate the level of force to which the implant 20 has been subjected. A lookup table may be used to calculate the force if the distance is known. Alternatively or additionally, an equation using parameters derived from correlating measured force and distance of extension can be used to calculate the force based on the distance of extension.

Figure 12:
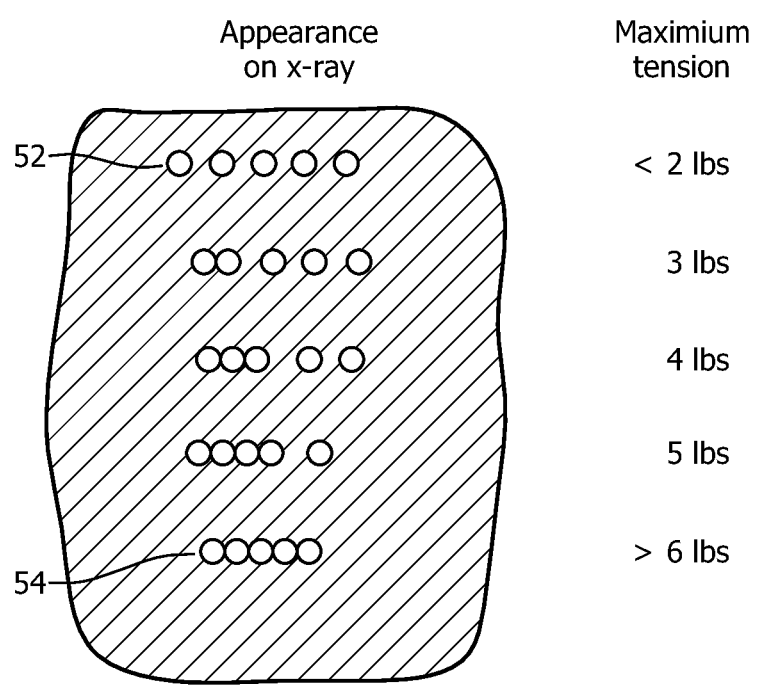
FIG. 12 illustrates a relationship between arrangements of the tension indicators and implant tension of the implant system in accordance with an embodiment of the present invention.

FIG. 12 illustrates an example of using the configuration or arrangement of the markers 40 to calculate the maximum tension to which the implant system 20 has been subjected. The arrangement of the markers 40 may be viewed using x-ray. As shown in FIG. 12, arrangements in which more markers 40 are compressed indicate higher tension. For example, arrangement 52 indicates that the maximum tension was 2 lbs or less. However, arrangement 54, which has more markers 40 in a compressed state than arrangement 52, indicates that the maximum tension was 6 lbs. This illustration is provided as an example and is not intended to be limiting. It is contemplated that the configuration or arrangement of the markers 40 may be determined using x-ray fluoroscopy, or other imaging techniques, such as planar x-ray, ultrasound, magnetic resonance imaging (MRI), computed tomography (CT) scan, or any other observational methods.

In some embodiments, the markers 40 may be reset such that the markers 40 may return to their initial, default arrangement from their final arrangement indicating the maximum tension. The initial, default arrangement of the markers 40 is the arrangement the markers 40 were in before the connecting portion 28 has been extended. In one embodiment, a second tether (not shown) may be provided on the implant system 20 to "tug" the markers 40 in the opposite direction of motion encountered during the extension of the implant system 20. That is, the second tether may pull the markers 40 in the opposite direction of A. The second tether may be connected to each marker 40, and the connection to each marker 40 may be configured or sized such that gaps can be provided between each of the markers 40 when the markers 40 are pulled back to their initial positions. Accordingly, when the second tether pulls the markers 40 in the opposite direction of A, the markers 40 may move in the direction opposite of A and may be returned to their initial configuration wherein the markers 40 are arranged with gaps or spaces separating the markers 40. As a result, the markers 40 are no longer in the "compressed" arrangement that indicate maximum tension. Instead, the markers 40 are returned to their initial, default arrangement.

This resetting capability may be used when implant system 20 titration is performed occasionally on the implant system 20. For example, after the implant system 20 has been used and extended over a period of time due to excess tension, the clinician or other healthcare provider may analyze the maximum tension to which the implant device 20 has been subjected. The clinician or healthcare provider may then titrate the implant system 20 based on the maximum tension indicated by the final arrangement of the markers 40. After titration, the markers 40 may then be reset to their initial, default position. This resetting capability can also help determine if each titration was successful and if the implant system 20 is functioning properly.

It is contemplated that the above examples of the markers 40 are not intended to be limiting. For example, the markers 40 may be external to the elastic portion 32, incorporated into the elastic portion 32, or may be a feature of the elastic portion 32, such as a material used to create the elastic portion 32. In embodiments where the elastic portion 32 includes a spring 36 or 48, the markers 40 may be external to the spring 36 or 48, incorporated into the spring 36 or 48, or may be a feature of the spring 36 or 48, such as a material used to create the spring 36 or 48. Alternatively or additionally, materials that change properties when deformed, stretched, or moved may be used in the implant system 20 to determine the amount of tension to which the implant system 20 has been subjected. The deformation, stretch, or movement of such materials may be detected using external devices.

In some embodiments, the implant system 20 may use inductive techniques or technologies wherein the measuring device is powered at the time of measurement by external means, such as RFID technology. The implant system 20 may optionally be active implant devices having electromechanical sensors, signal conditioning and processing means, memory, and RF communication capability for sensing and communicating data.

In some embodiments, the implant system 20 may also be adjusted for each subject. As mentioned above, subjects may require different levels of tension relief based on their particular characteristics. Accordingly, the implant system 20 may be adjusted before, during, and/or after implantation (in vivo). The implant system 20 may include a titration device that enables the elastic portion 32 to be adjusted and the tension of the connecting portion 28 to be adjusted.

In one embodiment, the elastic portion 32 may be pre-tensioned before implantation. When the elastic portion 32 includes a torsion spring, the structure, arrangement, size, materials, and other features of the coils may be customized for the subject. This may be used to adjust the amount of force threshold necessary to extend the elastic portion 32 of the connecting portion 28. In one embodiment, the elastic portion 32 of the connecting portion 28 may be rendered inactive (or fixed in length). This may be accomplished by attaching a fixed portion (e.g., a threaded cylinder) to the spring 36 or incorporating a fixed portion into the spring 36.

In another embodiment, the sleeve 44 may include materials with certain durometers based on the patient's needs and characteristics. The capsule may be filled with, or formed from materials of different durometers to change the force-length relationship of the elastic portion 32. A surgeon could select from several durometer capsules during the time of implantation, for example.

Figure 13:
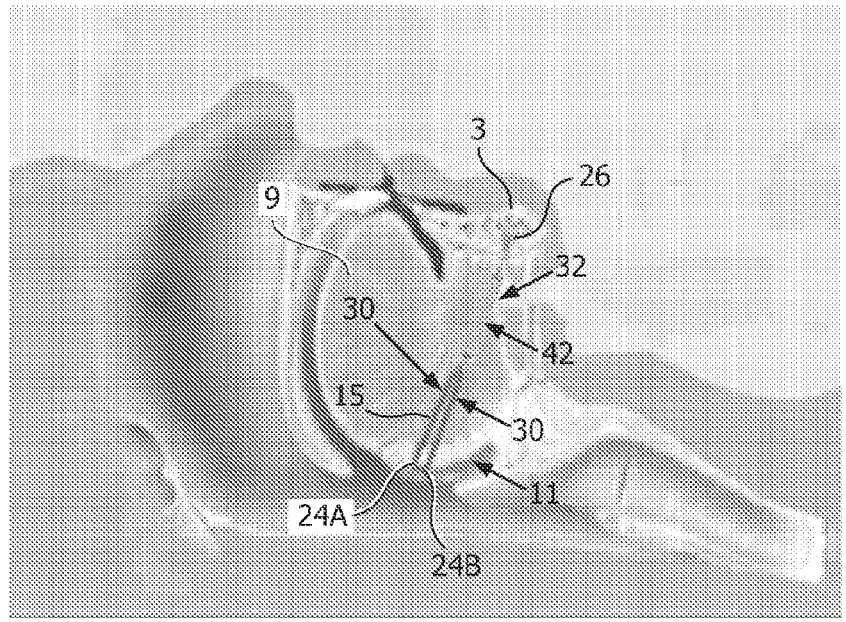
FIG. 13 illustrates a side sectional view of the implant system implanted within the patient in accordance with an embodiment of the present invention.

FIG. 13 shows an embodiment of the implant system 20 implanted within a subject. The bone screw 26 is engaged to the mandible of the subject. The connecting portion 28 includes the spring arrangement 42 forming the elastic portion 32 and tether loops 15 forming the inelastic portion 30. The portions of the tether 15 that are inserted through the tongue 9 to retain the tongue 9 define second portions 24A, 24B (two are shown in FIG. 13) of the implant system 20. In other words, in this embodiment, the second portions 24A, 24B include the portions of the tether 15 that are engaged to the tongue 9. The inelastic portions 30 of the implant system 20 include the portions of the tether 15 extending from the second portions 24A, 24B to the elastic portion 32. It is appreciated that the number of elastic portions 30 and inelastic portions 30 forming the connecting portion 28 may vary in other embodiments. It is also contemplated that in other embodiments, the second portions 24A, 24B may be defined by tissue anchors or other attachment mechanisms instead of portions of the tether 15 that are engaged to the tongue 9.

FIG. 14 shows another embodiment of the implant system 20 implanted within a subject. The bone screw 26 is engaged to the mandible 3 of the subject. In this embodiment, the bone screw 26 is connected to the second portion 24 using two tether sections 15 and two spring arrangements 42. The two tether sections 15 form the inelastic portion 30 of the connecting portions 28 and the two spring arrangements 42 form the elastic portion 32 of the connecting portions 28. Although the second portion 24 is not shown in this illustration, the second portion 24 may either include one or more attachment structures, such as tissue anchors 25, or may include portions of the tether 15 that are inserted through and engaged to the tongue (such as in the embodiment shown in FIG. 13). When the tension on the implant system 20 exceeds the predetermined threshold, the elastic portions 32, which includes the spring arrangements 42, extend to lengthen the connecting portions 28 so that the tension on the system 20 is relieved.

Figure 15:
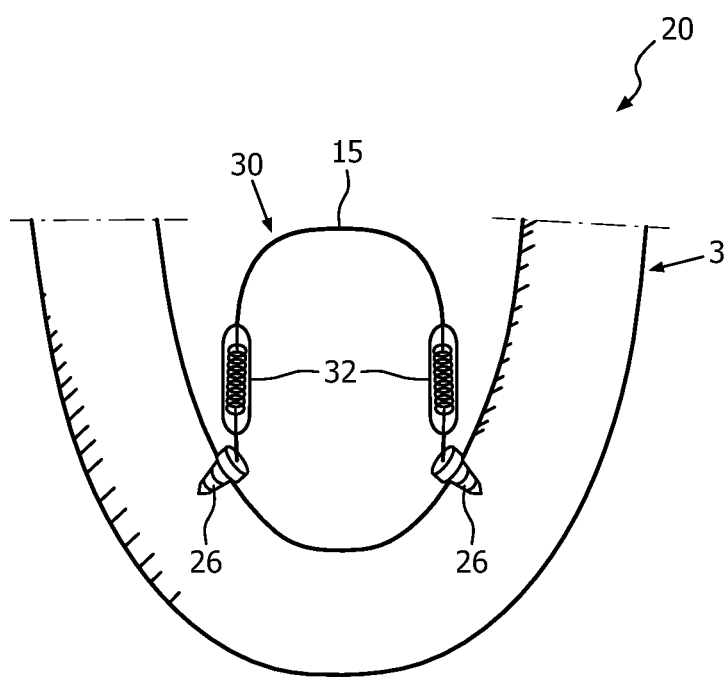
FIG. 15 illustrates another embodiment of the implant system.

FIG. 15 shows another embodiment of the implant system 20 implanted within a subject. In the illustrated embodiment, the implant system 20 includes the suture loop 15 and the elastic portions 32 provided on both sides thereof. The implant system 20 is anchored to generally the anterior and contralateral sides of the mandible 3 using bone screws 26.

The method of inserting the implant system 20 may be similar to methods known in the art. For the embodiment of the implant system 20 shown in FIG. 4, a clinician, surgeon, or other healthcare provider may secure the bone anchor 23 to the mandible of a patient using bone screws through apertures 34. A delivery device may be used to insert the tissue anchor 25 into the tongue percutaneously. The delivery device may contain a tube portion that retains the tissue anchor 25 until the tissue anchor 25 is ready to be deployed. In one embodiment, the delivery device may be configured to constrain the barbs, hooks, or attachment structures of the tissue anchor 25 until the tissue anchor 25 has been placed in the desired location, at which point the attachment structures are deployed to engage the surrounding tissue. An adjustment tool may be used to titrate the degree of tongue advancement by adjusting or rotating the locking spool mechanism housed in bone anchor 23, resulting in elongation or shortening of tether segment 15.

For the embodiment shown in FIG. 13, a bone screw inserter may be used to insert the bone screw 26 through a small submental incision. The inserter may then be manipulated towards a predetermined site to insert the screw 26 into the mandible 3. The elastic portion 32 may be attached to the bone screw 26. Using surgical techniques, a roughly triangular suture loop 15 is created in the base of the tongue. A suture passer (not shown) can be employed, for example, to create a segment that is placed laterally through the posterior section of the tongue 24A to 24B.

The connecting portion 28 may include an elastic portion 30 and two inelastic portions 30. Accordingly, the inelastic portion 30 and the elastic portion 32 form a triangular configuration through at least a portion of the tongue. As a result, the base of the tongue is stabilized and the potential for prolapse of the base of tongue is minimized. The inelastic portion 30 of the connecting portion 28 retains the tongue in a position away from the airway. However, when extreme forces are applied to the system 20, such as during swallowing, the elastic portion 32 of the connecting portion 28 may extend to accommodate such forces.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

The invention claimed is:

1. A glossoplasty implant tension relief system, comprising:
a first portion configured to engage a mandible of a subject;
a second portion configured to engage a tongue of the subject to retain at least a portion of the tongue of the subject;
a connecting portion configured to connect the first portion and the second portion, the connecting portion constructed and arranged to provide tension between the first portion and the second portion, the connecting portion comprising an elastic portion configured to provide elasticity between the first portion and the second portion;
a tension indicator operatively associated with the connecting portion configured to indicate an amount of force applied to the system by the tongue of the subject while the first portion is engaging the mandible of the subject, the second portion is engaging the tongue of the subject, and the connecting portion is providing tension between the first portion and the second portion, wherein
the tension indicator comprises one or more markers configured to move from an initial position to a second position responsive to an extension of the connecting portion, and wherein movement from the initial position to the second position indicates the amount of force applied to the system by the tongue.

2. The system of claim 1, wherein the elastic portion comprises a tension spring.

3. The system of claim 2, wherein the tension spring is encapsulated in a flexible sleeve.

4. The system of claim 1, wherein the tension indicator comprises a slideable structure constructed and arranged to slide along or with the elastic portion.

5. The system of claim 4, wherein an arrangement of the slideable structure indicates the amount of force applied to the system by the tongue of the subject.

6. The system of claim 1, wherein the elasticity provided by the elastic portion is adjustable.

7. The system of claim 6, wherein the elasticity is adjusted by rendering portions of the elastic portion inactive.

8. The system of claim 1, wherein the elastic portion comprises a torsion spring constructed and arranged to be retained at or near the first portion.

9. The system of claim 1, wherein the tension indicator includes one or more radio-opaque markers.

10. A method for indicating an amount of force applied by a tongue of a subject to an implantable system, the method being implemented using the implantable system including a first portion, a second portion, a connecting portion, and a tension indicator, the method comprising:
engaging the first portion with a mandible of the subject;
engaging the second portion with a tongue of the subject to retain at least a portion of the tongue;
providing tension between the first portion and the second portion, wherein tension is provided by the connecting portion, the connecting portion comprising an elastic portion having a level of elasticity; and
indicating, with the tension indicator, an amount of tension applied to the implantable system by the tongue of the subject while the first portion is engaging the mandible of the subject, the second portion is engaging the tongue of the subject, and the connecting portion is providing tension between the first portion and the second portion, wherein
the tension indicator comprises one or more markers configured to move from an initial position to a second position responsive to an extension of the connecting portion, and wherein movement from the initial position to the second position indicates the amount of force applied to the system by the tongue.

11. The method of claim 10, wherein the elastic portion comprises a tension spring.

12. The method of claim 11, wherein the tension spring is encapsulated in a flexible sleeve.

13. The method of claim 10, wherein indicating the amount of force includes sliding of a slideable structure along or with the elastic portion.

14. The method of claim 13, wherein an arrangement of the slideable structure indicates the amount of force applied to the system by the tongue of the subject.

15. The method of claim 10, further comprising adjusting the level of elasticity of the elastic portion.

16. The method of claim 15, wherein adjusting the level of elasticity comprises rendering portions of the elastic portion inactive.

17. The method of claim 10, wherein the elastic portion comprises a torsion spring constructed and arranged to be retained at or near the first portion.

18. A glossoplasty implant tension relief system, comprising:
- a first portion configured to engage a mandible of a subject;
- a second portion configured to engage a tongue of the subject to retain at least a portion of the tongue of the subject;
- a connecting portion configured to connect the first portion and the second portion, the connecting portion constructed and arranged to provide tension between the first portion and the second portion, the connecting portion comprising an elastic portion configured to provide elasticity between the first portion and the second portion;
- a tension indicator operatively associated with the connecting portion configured to indicate an amount of force applied to the system by the tongue of the subject, wherein the tension indicator includes one or more radio-opaque markers are configured to be used to detect the amount of force applied to the system by the tongue of the subject.

19. An implantable system configured to indicate an amount of force applied by a tongue of a subject to the implantable system, comprising:
- first means for engaging the implantable system with a mandible of the subject;
- second means for engaging the implantable system within the tongue of the subject to retain at least a portion of the tongue;
- means for providing tension between the first means and the second means, comprising an elastic portion; and
- means for indicating an amount of force applied to the implantable system by the tongue of the subject while the first means is engaging the mandible of the subject, the second means is engaging the tongue of the subject, and the means for providing tension is providing tension between the first means and the second means, wherein the means for indicating an amount of force comprises one or more markers configured to move from an initial position to a second position responsive to an extension of the means for providing tension, and wherein movement from the initial position to the second position indicates the amount of force applied to the system by the tongue.

20. A method for indicating an amount of force applied by a tongue of a subject to an implantable system, the method being implemented using the implantable system including a first portion, a second portion, a connecting portion, and a tension indicator, the method comprising:
- engaging the first portion with a mandible of the subject;
- engaging the second portion with a tongue of the subject to retain at least a portion of the tongue;
- providing tension between the first portion and the second portion, wherein tension is provided by the connecting portion, the connecting portion comprising an elastic portion having a level of elasticity; and
- indicating, with the tension indicator, an amount of tension applied to the implantable system by the tongue of the subject, wherein the tension indicator includes one or more radio-opaque markers configured to be used to detect the amount of force applied to the system by the tongue of the subject.

21. An implantable system configured to indicate an amount of force applied by a tongue of a subject to the implantable system, comprising:
- first means for engaging the implantable system with a mandible of the subject;
- second means for engaging the implantable system within the tongue of the subject to retain at least a portion of the tongue;
- means for providing tension between the first means and the second means, comprising an elastic portion; and
- means for indicating an amount of force applied to the implantable system by the tongue of the subject, wherein the means for indicating include one or more radio-opaque markers configured to be used to detect the amount of force applied to the system by the tongue of the subject.

* * * * *